United States Patent [19]

Sayigh et al.

[11] 4,008,275
[45] Feb. 15, 1977

[54] PROCESS FOR ISOLATING 4,4'-DIAMINODIPHENYLMETHANE

[75] Inventors: Adnan A. R. Sayigh, North Haven; Kwok K. Sun, Hamden; Henri Ulrich, Northford, all of Conn.

[73] Assignee: The Upjohn Company, Kalamazoo, Mich.

[22] Filed: Aug. 18, 1975

[21] Appl. No.: 605,752

[52] U.S. Cl. .................. 260/570 D; 260/570.8 R; 260/575; 260/578
[51] Int. Cl.² ........................................ C07C 85/26
[58] Field of Search .................. 260/570 D, 570 R

[56] References Cited

UNITED STATES PATENTS

| | | | |
|---|---|---|---|
| 2,943,112 | 6/1960 | Popoff et al. .................... 260/576 |
| 3,245,924 | 4/1966 | Cox et al. ........................ 260/570 X |
| 3,359,317 | 12/1967 | Krimm et al. .................... 260/577 |
| 3,362,979 | 1/1968 | Bentleg ............................ 260/570 X |
| 3,365,347 | 1/1968 | Lund et al. ...................... 260/570 |
| 3,424,795 | 1/1969 | Lund et al. ...................... 260/570 |
| 3,676,497 | 7/1972 | Recchio et al. .................. 260/570 |
| 3,857,890 | 12/1974 | Recchio et al. .................. 260/570 |

*Primary Examiner*—Robert V. Hines
*Attorney, Agent, or Firm*—Denis A. Firth; John Kekich

[57] ABSTRACT

2,2'- and 2,4'-diaminodiphenylmethane are selectively removed from admixtures thereof with the 4,4'-isomer by heating the isomer mixture at 30° to 100° C in the presence of styrene, α-alkylstyrenes, or the mono- or diamino nuclear substituted derivatives thereof and a catalyst (mineral acid, clays, diatomaceous earth, zeolites). The styrene or α-alkylstyrene can be employed as such or generated in situ from a precursor therefor. The process is particularly useful in facilitating the isolation of substantially pure 4,4'-diaminodiphenylmethane from the polyamine mixture obtained by condensation of aniline and formaldehyde.

15 Claims, No Drawings

PROCESS FOR ISOLATING 4,4'-DIAMINODIPHENYLMETHANE

BACKGROUND OF THE INVENTION

1. Field of the Invention

This invention relates to the preparation of diamines and is more particularly concerned with the selective removal of 2,2'- and 2,4'-diaminodiphenylmethane from admixture with 4,4'-diaminodiphenylmethane.

2. Description of the Prior Art

The condensation of aniline with formaldehyde in the presence of catalysts such as mineral acids, siliceous materials and the like, is well-known in the art; see, for example, U.S. Pat. Nos. 2,638,730; 2,950,263; 3,260,751; 3,277,173; 3,297,759; 3,362,979; and 3,476,806. The principal component of the product of this condensation is di(aminophenyl)methane the remaining components being oligomeric methylene polyphenyl polyamines, e.g. triamines, tetramines, etc. The proportion of diamine present in the mixture depends largely upon the molar proportion of aniline to formaldehyde. In general, the higher the proportion of aniline to formaldehyde, the higher the proportion of diamine in the product. The majority of the diamine is obtained as the 4,4'-isomer, the 2,4'-isomer being present in relatively minor proportion together with very small amounts of the 2,2'-isomer. The proportion of the isomers in any given product is dependent upon the reactant proportion and conditions employed in the reaction.

To date, no process has been devised which will give a product containing diamine which is exclusively in the form of the 4,4'-isomer. Proportions of 4,4'-isomer as high as 98 percent, and as low as 40 percent or less, have been reported. However, for many purposes, particularly where the diamine is to be used as an intermediate in the preparation of linear polyamides, polyimides, and similar polymers, it is desirable, if not essential, that the diamine be substantially pure 4,4'-isomer, i.e. that the content of 2,2'- and/or 2,4'-isomer be only 2 percent by weight or less.

Accordingly, the diamine isolated from the aniline-formaldehyde condensation (or the corresponding diisocyanate obtained by phosgenation of the diamine alone or as part of the mixture of polyamines obtained in the condensation) has been purified by conventional techniques such as fractional distillation, fractional crystallization, and the like, to achieve the desired purity of the 4,4'-isomer. Not only are such techniques tedious and expensive to operate on a commercial scale but they produce, as by-product, the 2,4'-isomer, or fractions enriched in the 2,4'-isomer, which are of much less utility than the 4,4'-isomer.

We have now found that the 2,2'- and 2,4'-diaminodiphenylmethanes can be selectively removed from a mixture of said isomer with 4,4'-diaminodiphenylmethane by a process which will be described below. This process can be applied successfully to relatively pure mixtures of 2,2'-, 2,4'- and 4,4'-diaminodiphenylmethane as well as to mixtures of these diamines with oligomeric polyamines obtained in the condensation of aniline with formaldehyde.

SUMMARY OF THE INVENTION

The invention comprises a process for selectively removing 2,2'- and 2,4'-diaminodiphenylmethane from admixtures thereof with 4,4'-diaminodiphenylmethane which process comprises heating said mixture of diamines at 30° to 100° C in the presence of (i) a compound of the formula:

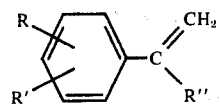

wherein R and R' are each independently selected from the group consisting of hydrogen and amino and R'' is selected from the class consisting of hydrogen and alkyl from 1 to 4 carbon atoms, inclusive, and (ii) a catalyst selected from the group consisting of aqueous mineral acid, clays, diatomaceous earths and zeolites.

In addition to processes in which the compound (I) is introduced as such into the reaction mixture, the process of the invention also contemplates processes in which precursors (as hereinafter defined and exemplified) are employed which serve to generate the compound (I) in situ.

The mixtures of 2,2'-, 2,4'- and 4,4'-diaminodiphenylmethanes employed in the above process can be substantially pure, i.e. free from oligomeric polyamines or the mixtures of isomers can be present in admixture with oligomeric polyamines as in the case of the mixtures isolated from the reaction product of aniline and formaldehyde under conditions well-known in the art, supra.

DETAILED DESCRIPTION OF THE INVENTION

The process of the invention is carried out conveniently by bringing the reactants together, in any order, and heating the resulting mixture at a temperature within the range of about 30° to about 100° C until routine analytical procedures, carried out on an aliquot, indicate that removal of the 2,2'- and 2,4'-isomers of the diamine has proceeded to the required extent. The exact procedure employed in carrying out the reaction in any given case depends upon the nature of the catalyst employed. Thus, when the catalyst is aqueous mineral acid, it is convenient to dissolve the mixture of diamines, employed as the starting material, in the aqueous acid and add the compound (I) to the resulting solution.

On the other hand where the catalyst employed in the process of the invention is a solid catalyst such as clay, zeolite or diatomaceous earth, the mixture of diamines and the compound (I) are brought together, optionally in the presence of an inert organic solvent such as chlorobenzene, dichlorobenzene, nitrobenzene, and the like, and the resulting mixture or solution is brought into contact with the solid catalyst in any appropriate fashion. For example, the solid catalyst is added to the mixture of diamines and compound (I) and the mixture is stirred at the appropriate temperature in a batch type vessel. Alternatively, as will be discussed in more detail hereafter, the solid catalyst is suspended in a column and the reactant solution is allowed to percolate through the column. The column and/or the solution can be preheated to temperatures within the range set forth above prior to being brought into contact with each other.

The aqueous mineral acids employed in the process of the invention are inclusive of hydrochloric, hydrobromic, sulfuric, and phosphoric acids. The preferred acid is aqueous hydrochloric acid.

As set forth above, the solid catalysts employed in the process of the invention include diatomaceous earths, zeolites and clays.

The diatomaceous earths are a well-known class of siliceous materials derived from diatoms and are inclusive of kieselguhr, tripolite, diatomite, infusorial earth and the like.

The clays employed in the process of the invention can be any of the clays conventionally employed in the catalytic art. Such clays include the naturally occurring and synthetic alumina silicates and are a well-recognized class of materials. Illustrative of such clays are: attapulgus clay, kaolins and montmorillonitic clays including fuller's earth, bentonite, montmorillonite and the like.

A wide variety of such clays is available commercially. For example, kaolin clays in various particle sizes are available from the J-M. Huber Corporation, Huber, Ga, and from Air Products and Chemicals, Inc. Bentonite clays in a variety of grades are available from the Georgia Kaolin Company, or under the trade name Filtrol from the Filtrol Corporation, Los Angeles, Calif. Montmorillonite clays mined in South Central Texas are available under the trade name Impact from The Milwhite Company, Houston, Tex.

The clays can generally be used in the state in which they are available commercially without any further treatment. However, it is generally found desirable to subject the clays to a drying process prior to use. Such drying can be accomplished by heating the clay, advantageously under nitrogen or under reduced pressure, to a temperature within the range of about 100° to 500° C to remove some, or the bulk, of the occluded water in the clay.

A particularly preferred clay for use in the process of the invention is attapulgus clay.

The natural and synthetic zeolites, employed as catalysts in the process of the invention, are also a well-recognized class of materials. The synthetic zeolites are described, for example, in R. W. Grimshaw, The chemistry and Physics of Clays, Fourth Edition Revised, 1971, pp. 168–9, Ernest Benn, Limited, London, and in D. W. Breck, Zeolite Molecular Sieves, John Wiley and Sons, New York. The zeolites are hydrated aluminosilicates having a relatively open crystal lattice which can be readily synthesized and which can be subjected to cation exchange to produce forms having different cations. Any of these known zeolites, in any of the different cation states, can be employed in the process of the invention. The naturally occurring zeolites are sodium and calcium aluminosilicates such as anocite, chabazite, heulandite, notrolite, stilbite, faujasite, and thomsonite; see, for example, Encyclopedia of Chemical Technology, Vol. 12, p. 295, 1954, Interscience Publishers Inc., New York, N.Y. A particularly useful group of zeolites for use in the present invention is the group of synthetic X and Y zeolites.

Advantageously the diatomaceous earth, clays or zeolites used in the process of the invention are employed in powder form. By this is meant that the average particle size of the solid catalyst is advantageously below about 20 microns (or above 65 mesh). A number of the solid catalysts of the invention are available in the form of pellets of various sizes, as extrudates, and as irregular granules, and such forms are particularly useful for continuous flow reactions which will be described hereinafter.

While any of the catalysts described and exemplified above can be employed in the process of the invention, it is preferred to employ aqueous mineral acids and more particularly hydrochloric acid, as the catalyst for reasons of economics and of overall efficiency and ease of operation. The mineral acid is preferably employed as an aqueous solution having a concentration within the range of about 0.1N to about 5N, and, preferably, within the range of about 1N to about 2N. The amount of mineral acid catalyst employed in the process of the invention is such that, for each equivalent of amine in the starting amine mixture, there is employed from about 0.5 to about 0.95 equivalents of acid. When the mixture of diamines employed as starting material is present in admixture with oligomeric methylene polyphenyl polyamines, the amine equivalents of the latter are included in calculating the amount of hydrochloric acid to be employed.

The proportion of the styrene (I) which is employed in the process of the invention varies according to the proportion of 2,2'- and 2,4'-isomers of diamine present in the starting material. Advantageously the proportion of the styrene (I) which is employed is in the range of about 0.01 mole to about 0.99 moles per mole of the total of 2,2'- and 2,4'-diaminodiphenylmethane present in the starting material. Preferably, the proportion of isopropenylbenzene (I) is from about 0.1 mole to about 0.6 moles per mole of the total of 2,2'- and 2,4'-diaminodiphenylmethane present in the starting material.

The styrenes represented by the formula (I) are inclusive of styrene itself, isopropenylbenzene α-ethylstyrene, α-propylstyrene, α-butylstyrene, the mono-amino nuclear substituted derivatives thereof such as p-aminostyrene, p-isopropenylaniline, p-amino-α-ethylstyrene, p-amino-α-butylstyrene, and the like, and the diamino nuclear substituted derivatives such as 4-isopropenyl-1,2-diaminobenzene, 5-isopropenyl-1,3-diaminobenzene, 3,5-diaminostyrene, 3,5-diamino-α-ethylstyrene, and the like. In addition to employing the compounds of formula (I) per se in the reaction process of the invention it is possible to form said compounds in situ by introducing a precursor of any of said compounds, which will generate one or more of the compounds (I) under the conditions prevailing in the reaction mixture. Illustrative of such precursors are (a) the dimers and homopolymers of p-isopropenylaniline and of the other mono and di-amino substituted derivatives of formula (I); (b) the carbinols of the formula

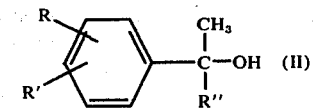

wherein R and R' and R" have the significance hereinbefore defined, and the lower-alkyl ethers of such carbinols which carbinols eliminate water, and the carbinol ethers eliminate the corresponding alcohol, under the conditions of the process of the invention to yield the corresponding compounds of formula (I); and (c) the benzylamines of the formula

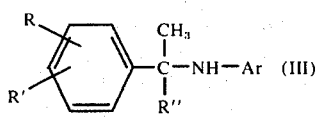

wherein R, R' and R'' have the significance hereinbefore defined and Ar is selected from the class consisting of phenyl and lower-alkyl substituted phenyl, which benzylamines split out a molecule of ArNH₂ under the conditions of the process of the invention to yield the corresponding compounds of formula (I).

The term "lower-alkyl" means alkyl from 1 to 6 carbon atoms, inclusive, such as methyl, ethyl, propyl, butyl, pentyl, hexyl, and isomeric forms thereof.

It has been found that, when the styrenes of formula (I) are generated in situ from the precursor carbinols of formula (II), it is desirable that one employ a catalyst other than clay in the process of the invention. Thus the water generated by conversion of the carbinol (II) to the styrene (I) generally greatly reduces the catalytic activity of the clays to a level which is undesirably low.

While any of the styrenes of formula (I) and precursors thereof set forth above can be employed in the process of the invention it is preferred to employ p-isopropenylaniline or a precursor thereof, particularly its dimers.

As set forth above, the mixture of isomeric diamines, catalyst, compound of formula (I) or precursor thereof and, optionally, the inert organic solvent is heated at a temperature in the range set forth above, advantageously with stirring, until the reaction is complete or has reached any desired stage. The progress of the reaction can be followed by routine analytical techniques performed on aliquots. Such techniques include gas liquid phase chromatography, thin layer chromatography, and the like. When the reaction has reached the desired stage, the diamines and oligomeric polyamines are isolated from the reaction mixture by conventional procedures. For example, when the reaction has been conducted in the presence of mineral acid, the latter is neutralized and the liberated amines are extracted using any appropriate inert organic solvent such as chloroform, methylene chloride and the like. The amines so extracted are purified, for example, by fractional distillation, fractional crystallization, and the like, to separate the essentially pure 4,4'-isomer of the diamine from the higher oligomeric amines.

Alternatively, when the reaction has been conducted in the presence of a solid catalyst it is merely necessary to separate the latter by filtration and purify the filtrate, after removal of any inert solvent, by the processes discussed above.

The by-products produced by conversion of the 2,2'- and 2,4'-isomers of the diamine in accordance with the process of the invention are oligomeric methylene polyphenyl polyamines. Such products are themselves useful, illustratively, as curatives for epoxy resins and as intermediates in that they can be phosgenated to form the corresponding polymethylene polyphenyl polyisocyanates. Indeed, in a particular embodiment, the total amine product from the process of the invention, i.e. the mixture of 4,4'-diaminodiphenylmethane and oligomeric methylene polyphenyl polyamines, is isolated as such and phosgenated, using conventional procedures, to the corresponding mixture of 4,4'-diisocyanatodiphenylmethane and oligomeric poly-methylene polyphenyl polyisocyanates. The mixture is useful as such in the preparation of rigid polyurethane and polyisocyanurate forms and in the preparation of adhesives, rigid non-cellular plastics and the like using techniques well-known in the art. Alternatively, the mixture can be subjected to fractional distillation using thin film evaporators, using techniques such as those described in U.S. Pat. No. 3,471,543, to isolate substantially pure 4,4'-diisocyanatodiphenylmethane. The latter is useful as an intermediate in the preparation of linear polyurethane elastomers using techniques well-known in the art.

As set forth above, the process of the invention can be applied to selectively remove 2,2'- and 2,4'-diaminodiphenylmethane contained in admixture with the 4,4'-isomer and/or with oligomeric methylene polyphenyl polyamines. In a particular embodiment, the process of the invention is applied to a mixture of 2,2'-, 2,4'- and 4,4'-diaminodiphenylmethanes which has been isolated as the forecut in the fractional distillation of 4,4'-diaminodiphenylmethane containing minor amounts of the 2,2'- and 2,4'-isomers, the latter having been isolated from the reaction product of aniline and formaldehyde using processes commercially employed in the art.

In carrying out the process of the invention it is found that the interaction of the compound of formula (I), whether employed as such or generated in situ as described above, with the 2,2'- and 2,4'-isomers of the di(aminophenyl)methane gives rise to mixed diamines and higher oligomers in which a p-aminophenyl group of the diamine or oligomer is replaced by the

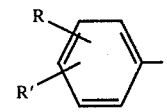

group of compound (I). This is of particular interest in the case of the compounds of formula (I) in which both R and R' represent amino. Thus the mixture of oligomers recovered from the reaction mixture obtained in this particular embodiment has a higher amino content than products derived using the compound (I) in which one or both of R and R' is hydrogen. Consequently the polyisocyanates derived by phosgenation of the oligomers in question have a lower isocyanate equivalent (i.e. a greater number of isocyanate groups per molecule) than those obtained from the oligomeric materials derived using compounds of formula (I) having R and/or R' = H.

The process of the invention has been described above largely in terms of a batch type procedure. However, as will be appreciated by one skilled in the art, the process of the invention can be carried out on a continuous basis. For example, the reaction mixture can be passed through a tubular reactor under conditions such that the mixture is maintained at the appropriate temperature for a residence time sufficient to ensure the desired removal of the 2,4'- and 4,4'-isomers. In the case of the solid catalysts, e.g. the zeolites, clays and diatomaceous earths, the latter can be packed in a column and the reaction mixture passed through the column at the appropriate temperature and with the appropriate residence time.

The styrenes (I) are well-known in the art as, for the most part, are the carbinols of formula (II) and the benzylamines of formula (III). The amino styrenes of formula (I) can be prepared, for example, by disproportionation of the appropriate di(aminophenyl)alkane using the procedure described by J. v. Braun et al. Annalen 472, 1, 1929, for the preparation of p-isopropenylaniline from 2,2'-di(4-aminophenyl)propane. The carbinols of formula (II) can be prepared by methods well-known in the art, for example, by reaction of the corresponding acetophenone with the appropriate alkylmagnesium iodide under Grignard conditions. In the case of the preparation of the carbinols of formula (II) wherein one or both of R and R' represent amino it is necessary to employ the corresponding acylaminoacetophenones in the reaction with the methyl magnesium iodide and to hydrolyze the acyl groups in a final step using procedures well-known in the art. The alkyl ethers of the carbinols (II) can be prepared by reaction of the tertiary halides derived from the latter with the appropriate alkali metal alkoxide. The benzylamines of formula (III) can be prepared, for example, by reacting the appropriate aniline $ArNH_2$, wherein Ar has the significance hereinbefore defined with the appropriate α-methyl-α-alkylbenzyl halide using the procedure described, for example, in Journal of the Chemical Society, 1970, pp. 1088–9.

The following examples describe the manner and process of making and using the invention and set forth the best mode contemplated by the inventors of carrying out the invention but are not to be construed as limiting.

EXAMPLE 1

A mixture of 2.5 g. (12.6 mmol.) of diaminodiphenylmethane (containing 1.5 percent by weight of the 2,2'-isomer, 10.5 percent by weight of 2,4'-isomer and 88 percent by weight of 4,4'-isomer), 6.5 ml. (20.0 mmol.) of 3.08N aqueous hydrochloric acid and 1.5 g. (12.8 mmol.) of isopropenylbenzene was heated at 95° to 100° C with stirring for 70 hr. The resulting mixture was made alkaline by the addition of 5N sodium hydroxide and was extracted with chloroform. The chloroform extract was dried over anhydrous sodium sulfate, filtered, and the filtrate evaporated to dryness. The residue was shown, by gas liquid phase chromatography using 2,2-di(4-aminophenyl)propane as internal standard, to contain a total of 1.66 g. (66 percent yield) of diaminodiphenylmethane containing 99.4 percent by weight of 4,4'-isomer and 0.6 percent by weight of 2,4'-isomer.

EXAMPLE 2

Using the procedure described in Example 1 but replacing the diaminodiphenylmethane used as starting material by 2.5 g. of a synthetic mixture of diaminodiphenylmethane containing 50 percent by weight of 4,4'-isomer and 50 percent by weight of 2,4'-isomer, and increasing the amount of isopropenylbenzene to 3.0 g. (25.6 mmol.), there was obtained a total of 0.65 g. (26 percent yield) of 4,4'-diaminodiphenylmethane containing less than 10 percent of 2,4'-isomer.

EXAMPLE 3

A mixture of 1.0 g. (5.05 mmol.) of diaminodiphenylmethane (containing 15 percent by weight of 2,4'-isomer and 85 percent of 4,4'-isomer), 8.0 ml. (8.0 mmol.) of N aqueous hydrochloric acid and 0.133 g. (1.0 mmol.) of p-isopropenylaniline (J. v. Braun et al., supra) was heated with stirring at 95° C for 1.5 hr. The resulting mixture was cooled to room temperature (circa 20° C), made alkaline by the addition of 5N sodium hydroxide, and extracted with chloroform. The chloroform extract was dried over anhydrous sodium sulfate, filtered and the filtrate evaporated to dryness. The residue was shown, by gas liquid phase chromatography, to contain 0.82 g. (82 percent theoretical yield) of diaminodiphenylmethane which was found (by gas liquid phase chromatography) to contain 99.4 percent of 4,4'-isomer and 0.6 percent of 2,4'-isomer.

EXAMPLE 4

Using the procedure described in Example 3 but replacing the diaminodiphenylmethane there used by an equal amount of a synthetic mixture of diaminodiphenylmethane containing equal parts by weight of 2,4'- and 4,4'-isomers, and increasing the quantity of p-isopropenylaniline used to 0.403 g. (3.03 mmol.) there was obtained a product containing 0.47 g. (47 percent yield) of diaminodiphenylmethane of which 98.2 percent by weight was 4,4'-isomer and 1.8 percent by weight was 2,4'-isomer.

EXAMPLE 5

A solution containing 1 g. (5.05 mmol.) of diaminodiphenylmethane (containing 15 percent by weight of 2,4'-isomer and 85 percent of 4,4'-isomer) and 0.233 g. (1.75 mmol.) of p-isopropenylaniline in 2.5 ml. of chlorobenzene was admixed with 0.5 g. of XZ-25 [a zeolite; Grace Davidson Chemical; previously heated at 495° C for 2.5 hr.] The resulting mixture was stirred and heated at 70° C for 3 hr. followed by heating under reflux (132° C) for 12.5 hr. At the end of this time the mixture was filtered, the zeolite was washed on the filter with chlorobenzene, and the filtrate and washings were evaporated to dryness. The residue was shown, by gas liquid phase chromatography, to contain 0.75 g (75 percent theoretical yield) of diaminodiphenylmethane of which 95.7 percent by weight was 4,4'-isomer and 4.3 percent by weight was 2,4'-isomer.

EXAMPLE 6

The procedure described in Example 5 was repeated with the sole exception that no chlorobenzene was included in the reaction mixture. The initial reaction temperature was 80° C for 1 hr. and then the mixture was heated at 150°± 2° C for 5 hours. At the end of this time the product was shown by gas liquid phase chromatography to contain 0.81 g. (81 percent theoretical yield) of diaminodiphenylmethane of which 95.3 percent by weight was 4,4'-isomer and 4.7 percent by weight was 2,4'-isomer.

EXAMPLE 7

A solution of 0.198 g. (1 mmol.) of diaminodiphenylmethane (containing 15 percent by weight of 2,4'-isomer and 85 percent by weight of 4,4'-isomer) and 0.0532 g. (0.2 mmol.) of the dimer of p-isopropenylaniline in 0.8 ml. of chlorobenzene was admixed with 0.1 g. of zeolite XZ-25. The resulting mixture was heated under reflux for 14 hr. at the end of which time the mixture was filtered and the filtrate was analyzed by gas liquid phase chromatography. The resulting diaminodiphenylmethane in the filtrate was found to contain 93.2 percent by weight of the 4,4'-isomer and 6.8 percent by weight of 2,4'-isomer.

The dimer of p-isopropenylaniline employed in the above experiment was obtained as follows:

A mixture of 2.4 g. (18 mmol.) of p-isopropenylaniline, 1.8 g. of zeolite XZ-25 (see Example 5; previously activated by heating at 495° C for 2.5 hr.), and 9.5 ml. of chlorobenzene was stirred and heated at 80° to 90° C for a total of 8.5 hr. The resulting mixture was filtered hot and the zeolite was washed on the filter with hot chlorobenzene. The combined filtrate and washings were cooled to room temperature and the crystalline solid which separated was isolated by filtration. There was thus obtained a mixture, having a melting point of 162° to 166° C, of dimers of p-isopropenylaniline having the formulae:

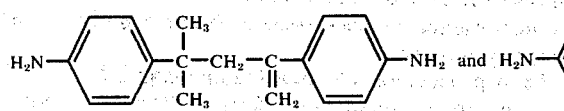 and 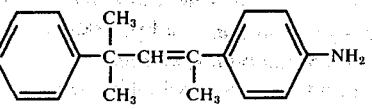

EXAMPLE 8

To a solution of 0.5 g. (2.5 mmol.) of di(aminophenyl)-methane [a synthetic mixture containing 20 percent by weight of the 2,4'-isomer and 80 percent by weight of the 4,4'-isomer] in 4.5 ml. (4.5 mmol.) of N-aqueous hydrochloric acid was added 0.212 g. (1 mmol.) of 1-(p-aminophenyl)-1-N-anilinoethane. The resulting mixture was stirred at 25° C for 4 hr. The product so obtained was neutralized using aqueous sodium hydroxide and the liberated amine was extracted in chloroform. The chloroform extract was dried and evaporated to dryness. The di(aminophenyl)methane in the residue was shown by gas liquid phase chromatography to contain 2.5 percent by weight of 2,4'-isomer and 97.5 percent by weight of 4,4'-isomer.

The 1-(p-aminophenyl)-1-N-anilinoethane employed in the above reaction was obtained as follows:

A mixture of 50 g. (0.3 mole) of p-nitroacetophenone, 80 g. (0.86 mole) of aniline, 120 g. of molecular sieves (4A: powdered) and 200 ml. of benzene was heated under reflux for 1 hr. The resulting product was filtered and the filtrate was evaporated and the residue was treated with 20 ml. of diethyl ether before being stored overnight in a refrigerator. Th solid which separated was isolated by filtration and recrystallized from a mixture of actone (1 part), diethyl ether (5 parts) and petroleum ether (2 parts). There was thus obtained 61.5 g. of the anil of p-nitroacetophenone. A solution of 2.40 g. (10 mmol.) of the latter compound in 100 ml. of diethyl ether and 50 ml. of ethyl acetate was hydrogenated in the presence of 1 g. of 5 percent palladium on barium sulfate catalyst. The theoretical amount of hydrogen was taken up in about 2 hr. The resulting product was filtered to remove catalyst and the filtrate was evaporated to dryness. Small amounts of aniline and p-aminobenzylamine were removed by distillation under reduced pressure and the residue was 1-(p-aminophenyl)-1-N-anilinoethane which was employed in the reaction described above without further purification.

EXAMPLE 9

To a solution of 0.5 g. (2.5 mmol.) of di(aminophenyl)methane (a synthetic mixture containing 20 percent by weight of 2,4'-isomer and 80 percent by weight of 4,4'-isomer) in 4.5 ml. (4.5 mmol.) of N aqueous hydrochloric acid was added 1 ml. of α, α-dimethylbenzyl alcohol (Eastman Organic Chemicals) and the mixture was stirred and heated at 95° C for 60 hr. At the end of this time the isomer ratio in the di(aminophenyl)methane was found by gas liquid phase chromatography to be 2.2 percent by weight of 2,4'-isomer and 97.8 percent by weight of 4,4'-isomer.

EXAMPLE 10

A mixture of 0.4 g. (2 mmol.) of di(aminophenyl)methane, 1 ml. of chlorobenzene, 0.152 g. (0.82 mmole). of p-aminostyrene and 0.20 g. of zeolite XZ-25 was heated with stirring for 7 hr. at 120° C. At the end of this time it is found by gas liquid phase chromatography that the 2,4'-isomer content in the diamine had been reduced to 10.9 percent by weight with a corresponding increase in 4,4'-isomer content to 89.1 percent by weight.

We claim:

1. A process for selectively removing 2,2'- and 2,4'-diaminodiphenylmethane from admixtures thereof with 4,4'-diaminodiphenylmethane which process comprises heating said mixture of diamines at 30° to 100° C in the presence of (i) a compound of the formula:

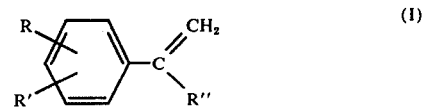 (I)

wherein R and R' are each independently selected from the group consisting of hydrogen and amino and R'' is selected from the group consisting of hydrogen and alkyl from 1 to 4 carbon atoms, inclusive, and (ii) a catalyst selected from the group consisting of aqueous mineral acid, clays, diatomaceous earths and zeolites.

2. A process according to claim 1 in which the compound of the formula (I) is isopropenylbenzene.

3. A process according to claim 1 in which the compound of the formula (I) is p-isopropenylaniline.

4. A process according to claim 1 in which the compound of the formula (I) is generated in situ by adding a member selected from the class consisting of the corresponding carbinols of the formula:

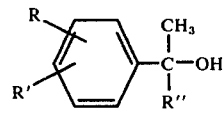

and the lower-alkyl ethers thereof, wherein R, R' and R'' are as defined in claim 1, to the reaction mixture.

5. The process according to claim 4 wherein the carbinol is α, α-dimethylbenzyl alcohol.

6. A process according to claim 1 in which the compound of the formula (I) is generated in situ by adding to the reaction mixture the corresponding benzylamine of the formula:

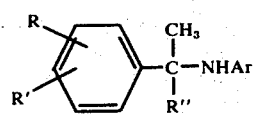

wherein R, R' and R'' are as defined in claim 1 and Ar represents an aromatic radical selected from the group consisting of phenyl and lower-alkyl substituted phenyl.

7. The process of claim 6 wherein the benzylamine is 1-(p-aminophenyl)-1-N-anilinoethane.

8. A process according to claim 1 in which the compound of the formula (I) is generated in situ by adding to the reaction mixture the corresponding dimer.

9. A process to according to claim 1 in which, when a solid catalyst is employed, there is also present an inert organic solvent.

10. A process according to claim 1 wherein the diaminodiphenylmethane employed as starting material is a mixture of 2,2'-, 2,4'- and 4,4'-diaminodiphenylmethane and oligomers which has been obtained by condensation of aniline and formaldehyde.

11. A process according to claim 10 wherein the diaminodiphenylmethane starting material is the forecut obtained in the fractional distillation of said mixture of diamines and oligomers.

12. A process for selectively removing 2,2'- and 2,4'diaminodiphenylmethane from admixtures thereof with 4,4'-diaminodiphenylmethane which process comprises heating said mixture of diamines at 30° to 100° C in the presence of aqueous hydrochloric acid and isopropenylbenzene.

13. A process for selectively removing 2,2'- and 2,4'-diaminodiphenylmethane from admixtures thereof with 4,4'-diaminodiphenylmethane which process comprises heating said mixture of diamines at 30° to 100° C in the presence of aqueous hydrochloric acid and p-isopropenylaniline.

14. A process for selectively removing 2,2'- and 2,4'-diaminodiphenylmethanes from admixtures thereof with 4,4'-diaminodiphenylmethane which process comprises heating said mixture of diamines at 30° to 100° C in the presence of zeolite and p-isopropenylaniline.

15. A process according to claim 1 in which the compound of formula (I) is p-aminostyrene.

* * * * *